(12) United States Patent
Eiermann et al.

(10) Patent No.: US 7,582,789 B2
(45) Date of Patent: Sep. 1, 2009

(54) IBANDRONATE POLYMORPH

(75) Inventors: Uwe Eiermann, Ladenburg (DE); Bernd Junghans, Edingen-Neckarhausen (DE); Bernhard Knipp, Kuerten-Olpe (DE); Tim Sattelkau, Ludwigshafen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 333 days.

(21) Appl. No.: 11/338,559

(22) Filed: Jan. 24, 2006

(65) Prior Publication Data

US 2006/0172976 A1 Aug. 3, 2006

(30) Foreign Application Priority Data

Feb. 1, 2005 (EP) .................. 05100687

(51) Int. Cl.
*C07F 9/02* (2006.01)

(52) U.S. Cl. .................................... 558/158

(58) Field of Classification Search ............. 558/158; 514/108

See application file for complete search history.

(56) References Cited

U.S. PATENT DOCUMENTS

| 4,927,814 A | 5/1990 | Gall et al. |
| 4,942,157 A | 7/1990 | Gall et al. |
| 2002/0006441 A1 | 1/2002 | Gabel et al. |
| 2006/0172975 A1 | 8/2006 | Eiermann et al. |
| 2007/0161606 A1* | 7/2007 | Bayer et al. ............ 514/102 |

FOREIGN PATENT DOCUMENTS

| EP | 252 504 | 1/1988 |
| EP | 1 121 375 B1 | 5/2003 |
| WO | WO 01/52859 A1 | 7/2001 |
| WO | WO 2006/002348 A2 | 1/2006 |
| WO | WO 2006/024024 A2 | 3/2006 |

OTHER PUBLICATIONS

Brittain, polymorphism in Pharmaceutical Solids, Drugs and the Pharmaceutical Science; 1999, V. 95, pp. 348-361.*
Bonviva European Public Assessment Report, Part 6, "Scientific Discussion", p. 2 (2004).
Britain, et al., *Polymorphism in Pharmaceutical Solids*, Polymorphism in Pharmaceutical Solids, 1999, pp. 235-238, XP002278123.
Dallas et al., Blood, 93, pp. 1697-1706 (1999).
*EMEA*, Bondronat, Scientific Discussion, (2004) p. 1-29.

* cited by examiner

*Primary Examiner*—Rei-tsang Shiao
(74) *Attorney, Agent, or Firm*—George W. Johnston; Patricia S. Rocha-Tramaloni; David E. Wildman (57) ABSTRACT

The present invention relates to a new crystalline polymorph of 3-(N-methyl-N-pentyl) amino-1-hydroxypropane-1,1-diphosphonic acid monosodium salt monohydrate (Ibandronate) with the following formula Formula 1

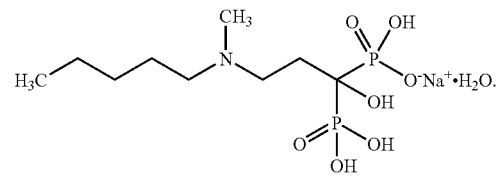

6 Claims, 6 Drawing Sheets

Figure 1: X-ray diffraction pattern of polymorph B

Figure 3: Ibandronat Raman-spectrum of polymorph B

IBANDRONATE POLYMORPH

PRIORITY TO RELATED APPLICATIONS

This application claims the benefit of European Application No. 05100687.2, filed Feb. 1, 2005, which is hereby incorporated by reference in its entirety.

The present invention relates to a new polymorph crystal form of 3-(N-methyl-N-pentyl) amino-1-hydroxypropane-1,1-diphosphonic acid monosodium salt monohydrate (Ibandronate) of the following formula Formula 1 and a process for its preparation.

Ibandronate is one of the most potent anti-resorptive drugs that directly inhibit osteoclast activity and present an effective pharmacologic alternative for controlling hypercalcemia of malignancy. Ibandronate binds to hydroxyapatite in calcified bone, rendering it resistant to hydrolytic dissolution by phosphatases, thereby inhibiting both normal and abnormal bone resorption. This drug increases bone mass and decreases the risk of fractures and is therefore particularly well adapted to bone and calcium metabolic diseases such as for instance osteoporosis or Paget's disease (EP-A 0252504).

It has been found that Ibandronate may exist in various polymorphs.

One polymorph of Ibandronate hereinafter also designated as polymorph A was identified as being thermodynamically more stable, whereas a second polymorph of Ibandronate, hereinafter designated as polymorph B, is easier to separate within the production process.

The ability of a substance to exist in more than one crystal form is defined as polymorphism and these different crystal forms are known as "polymorph modifications" or "polymorphs".

Polymorphism can influence many aspects of solid state properties of a drug. Different crystal modifications of a substance may differ considerably from one another in different physical properties which may influences directly their solubility for instance. Polymorphism is found in several organic compounds.

An exhaustive treatment of polymorphism in pharmaceutical and molecular crystals is given e.g. by H. G. Brittain in *Polymorphism in Pharmaceutical Solids*, H. G Brittain or, Marcel Dekker Inc., New York, 1999 and in *Solid-State Chemistry of Drugs*, SSCI Inc., West Lafayette; Ind., 1999.

An object of the present invention is to specifically isolate and characterize Ibandronate polymorph B and to develop a process for the preparation of Ibandronate polymorph B.

The object has been achieved with the identification of crystalline polymorph B of Ibandronate and with a process for its preparation as claimed in the present invention.

Unless otherwise indicated, the following definitions are set forth to define the meaning and scope of the various terms used and described in the description.

The term "Ibandronate polymorph B" refers to the polymorph crystal form of 3-(N-methyl-N-pentyl) amino-1-hydroxypropane-1,1-diphosphonic acid monosodium salt monohydrate as defined in the claims and the description of the present invention.

The term "crystalline polymorph" refers to a crystal modification which can be characterized by analytical methods such as e.g. X-ray powder diffraction, IR spectroscopy and Raman spectroscopy.

The term IR means infrared.

The crystalline Ibandronate polymorph B of the present invention can be characterized by an X-ray powder diffraction pattern having characteristic peaks expressed in angle 2-theta at approximately:

| Angle 2-theta | Intensity [%] |
| --- | --- |
| 9.7° | 0.6 |
| 12.2° | 1 |
| 14.4° | 0.6 |
| 16.8° | 1 |
| 25.8° | 1.8 |

Angle 2-theta includes an uncertainty of ±0.2 (expressed in degrees), 2-theta represents the reflection angle according to the Bragg law. A reflection at a glancing angle θ gives rise to a reflection at an angle 2θ to the direction of the incident beam.

Figure 1:
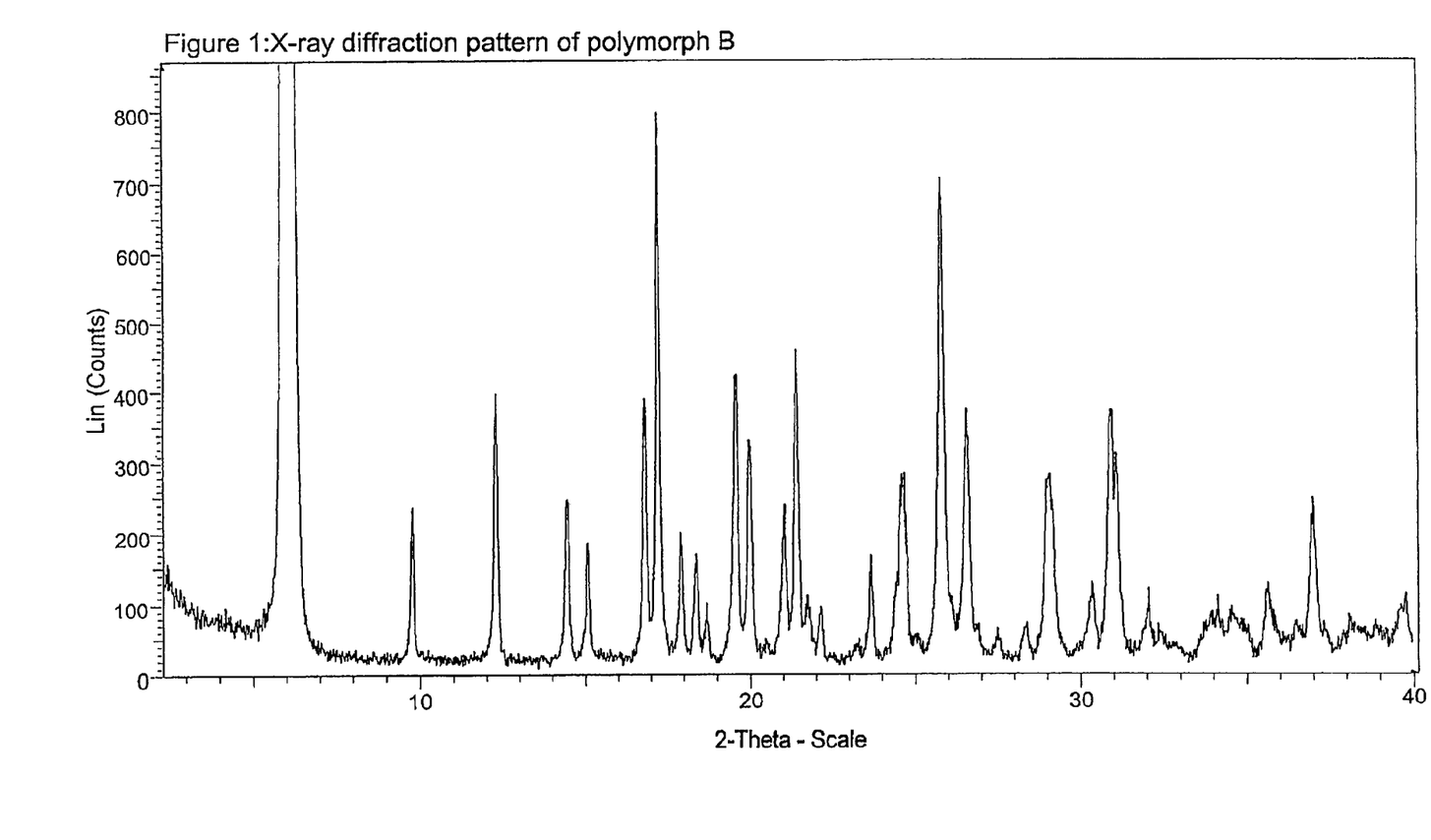
FIG. 1: shows an X-ray diffraction pattern of crystalline Ibandronate polymorph B as obtained in example 1.

The crystalline Ibandonate polymorph B as described above can further be characterized by the x-ray powder diffraction pattern as shown in FIG. 1.

The crystalline Ibandronate polymorph B can furthermore be characterized by its IR absorption spectrum having characteristic peaks expressed in $cm^{-1}$ at approximately:

| Bands [$cm^{-1}$] |
| --- |
| 3679 |
| 3164 |
| 2955 |
| 2854 |
| 1377 |
| 1290 |
| 1157 |
| 1093 |
| 1068 |
| 1035 |
| 965 |
| 951 |
| 933 |
| 905 |
| 761 |
| 723 |

The term approximately means in this context that the cm$^{-1}$ value can vary by ±4 cm$^{-1}$.

Figure 2:
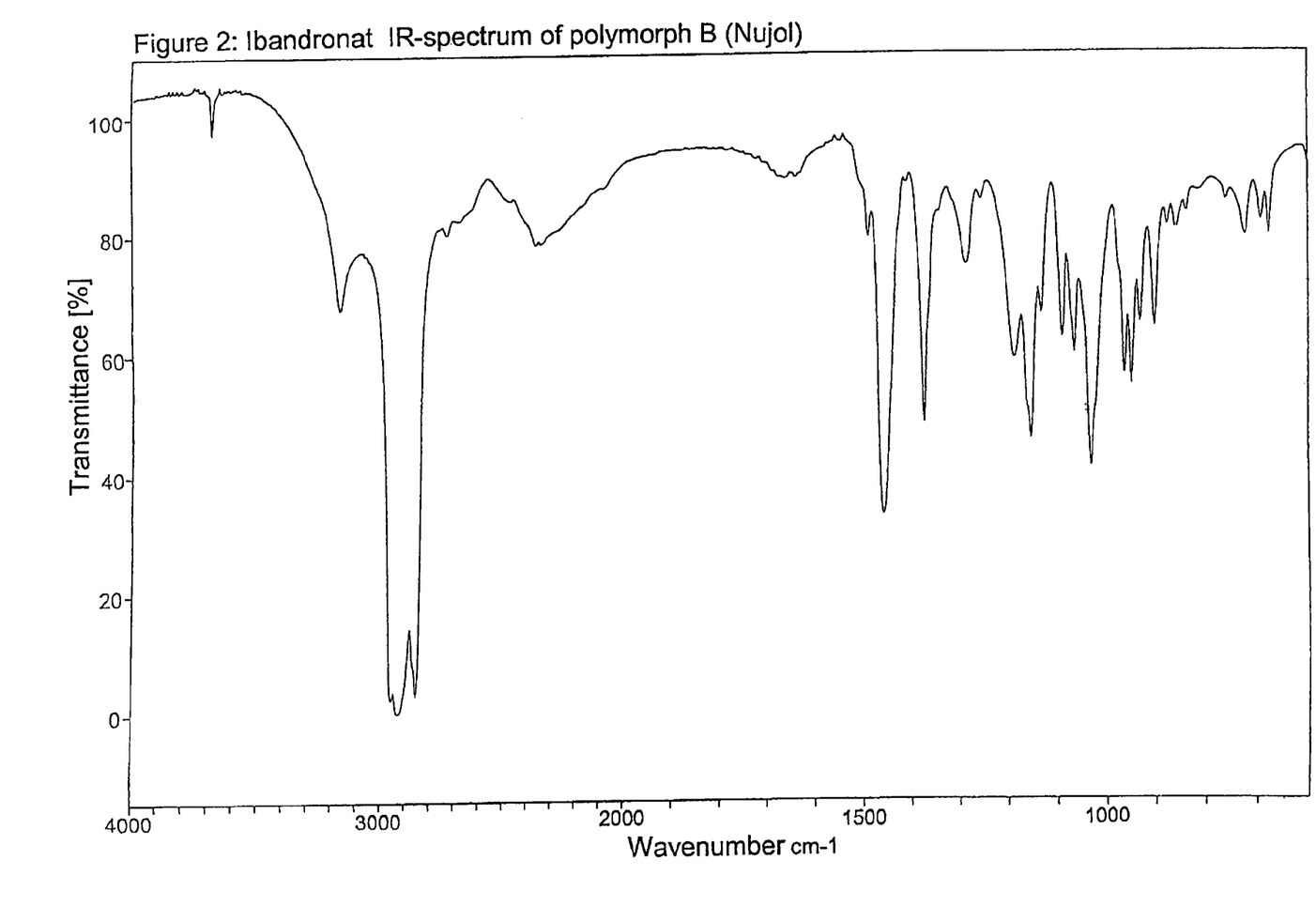
FIG. 2: shows an IR-spectrum of crystalline Ibandronate polymorph B

The crystalline Ibandronate polymorph B can further be characterized by the IR absorption spectrum shown in FIG. 2.

The crystalline Ibandronate polymorph B as described above can furthermore be described by Raman vibrational spectroscopy. The Raman spectrum has the following characteristic peaks expressed in cm$^{-1}$ at approximately:

| Bands [cm$^{-1}$] |
| --- |
| 2968 |
| 2951 |
| 2928 |
| 2887 |
| 2849 |
| 1441 |
| 1308 |
| 1136 |
| 1056 |
| 1023 |
| 954 |
| 907 |
| 839 |
| 762 |
| 678 |

The term approximately means in this context that the cm$^{-1}$ value can vary by ±8 cm$^{-1}$.

Figure 3:
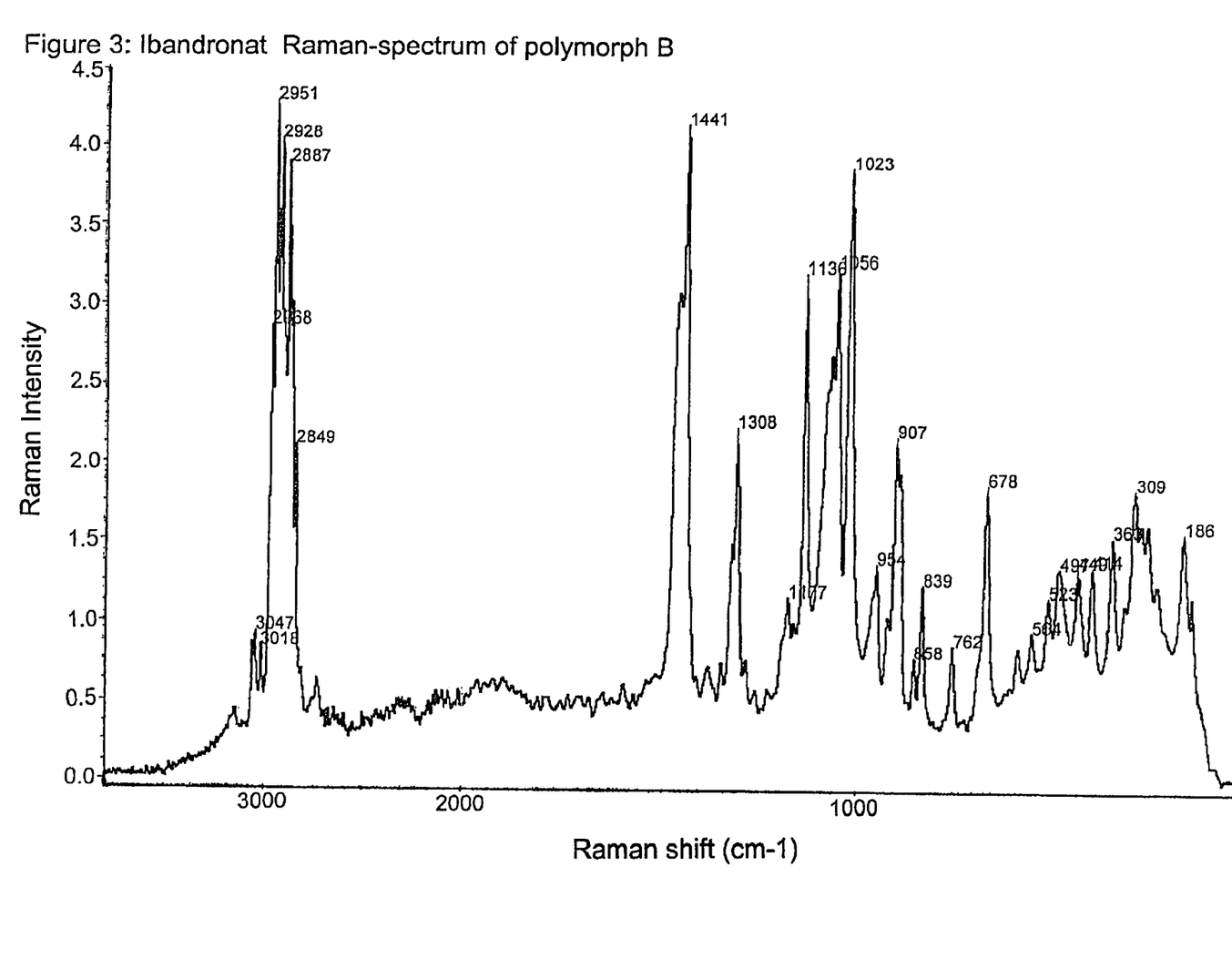
FIG. 3: shows a Raman spectrum of Ibandronate polymorph B

The crystalline Ibandronate polymorph B can further be characterized by the Raman spectrum shown in FIG. 3.

The crystalline Ibandronate polymorph B described above is further characterized by a solubility in water of about 279 g/l at 25° C. (with partial conversion to crystalline Ibandronate polymorph A).

The process according to the present invention is characterized by the crystallization of 3-(N-methyl-N-pentyl) amino-1-hydroxypropane-1,1-diphosphonic acid monosodium salt or a monohydrate, a polymorph or a mixture of polymorphs thereof at a temperature of 10° C. to 45° C. in a polar solvent using the addition of a polar aprotic solvent to initialize the crystallization.

A solvent such as water may be used as the polar solvent to which the polar aprotic solvent is added to initiate crystallization.

Some suitable polar aprotic solvents are aliphatic ketones such as acetone or methyl ethyl ketone or cyclic ethers like tetrahydrofuran or dioxane. Preferred polar aprotic solvents are acetone and tetrahydrofuran, where tetrahydrofuran is the most preferred.

Preferably the crystallization takes place at a temperature of about 35° C., maintained for about 15 minutes to about 120 minutes.

Starting product for the process of the present invention can either be the 3-(N-methyl-N-pentyl) amino-1-hydroxypropane-1,1-diphosphonic acid monosodium salt e.g. obtained from a process as outlined in reference example 1, or crystalline Ibandronate polymorph A e.g. obtained according to reference example 2, or a mixture of crystalline Ibandronate polymorph A with crystalline Ibandronate polymorph B.

The starting product can either be dissolved in the polar solvent at about room temperature and then be warmed to the crystallization temperature or alternatively be dissolved at a higher temperature and then be cooled to the crystallization temperature as indicated above.

Ethanol residues which may be present from the manufacturing process (according to reference example 1) can easily be removed by known methods e.g. by distilling the ethanol off as azeotrope.

Crystallization as a rule occurs spontaneously but can also be initiated by addition of crystals of Ibandronate polymorph B.

The crystal suspension so obtained may be cooled under stirring until crystallization is complete before the filtration takes place.

The whole crystallization process may be controlled regarding temperature, heating and cooling periods with equipment common to the skilled practitioner.

Separation of the desired polymorph can be effected by common filtration techniques. As a rule the precipitate is washed with the polar solvent used for the crystallization, preferably with a mixture of water and acetone in a ratio of about 1:1 (V/V).

Drying of the crystalline Ibandronate polymorph B preferably happens at a temperature from 30° C. to 60° C. for about 24 hours to 72 hours either at normal or at reduced pressure.

The Ibandronate can be obtained with a content of the crystalline Ibandronate polymorph B of at least 80%.

The crystalline Ibandronate polymorph B of the present invention can be used as a pharmaceutically active compound which acts as an efficient anti-resorptive drug that directly inhibits osteoclast activity and thus also increases bone mass. Accordingly this polymorph can be used for the treatment and/or prevention of diseases which are associated with bone and calcium metabolic disease such as for instance osteoporosis or Paget's disease.

The invention therefore also relates to pharmaceutical compositions comprising a crystalline Ibandronate polymorph B as defined above and a pharmaceutically acceptable carrier and/or adjuvant.

The invention also encompasses a crystalline Ibandronate polymorph B as described above for use as therapeutically active substances.

The following examples serve as illustration of the invention.

EXAMPLES

X-Ray Powder Diffraction Measurement Method

Figure 4:
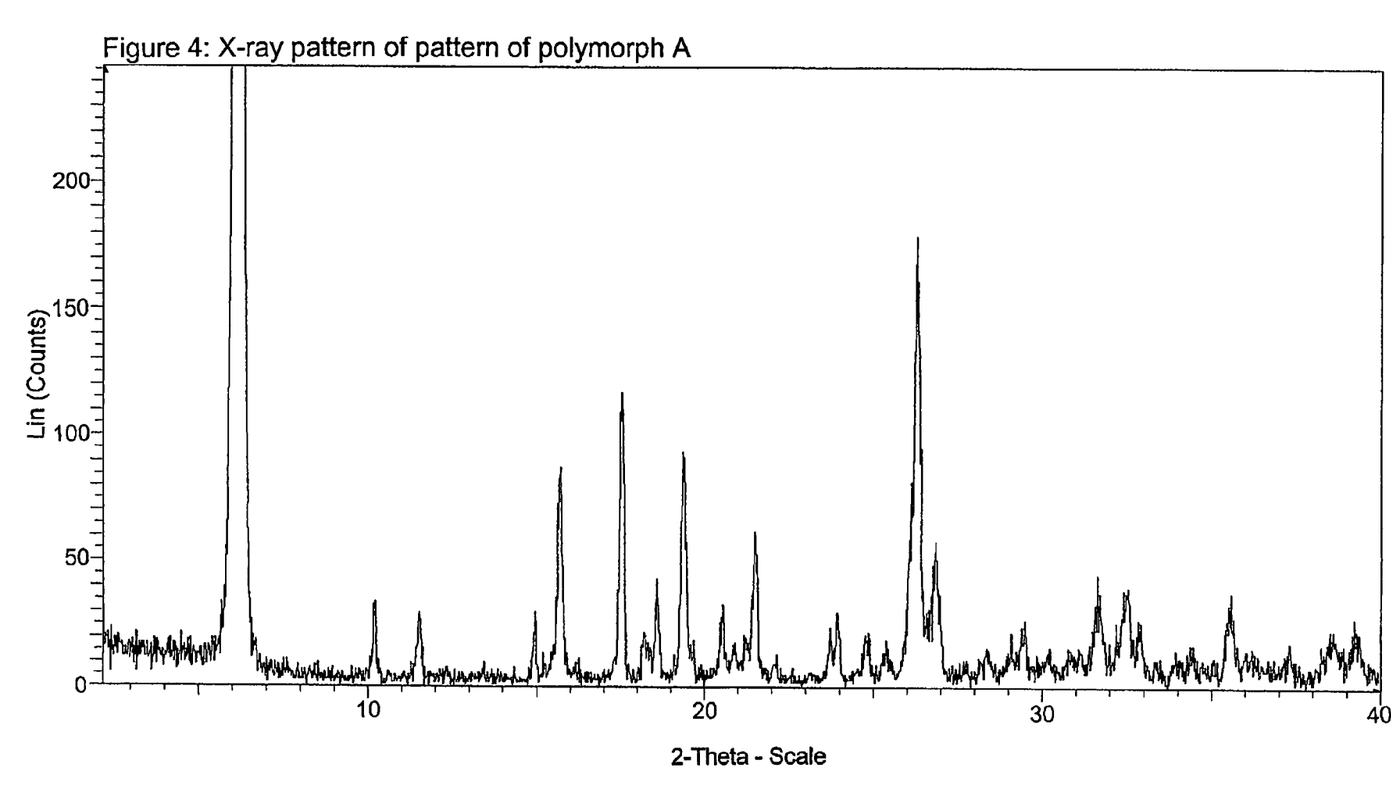
FIG. 4: shows an X-ray diffraction pattern of crystalline Ibandronate polymorph A as obtained in Ref. example 2.

The x-ray powder diffraction patterns of the individual crystalline Ibandronate polymorphs A and B were recorded with a Bruker D8 Advance AXS diffractometry (geometry: Bragg-Brentano; radiation: CuKα in the angle range 2θ=2° to 40°; Cu secondary monochromator; step scan with 0.02° and a measuring time of e.g. 4.0 s per step). The samples weighing approximately 500 mg were prepared into carrier wells and exposed to CuKα radiation. Radiation diffracted at the lattice levels is converted into electronic signals by a scintillation counter and processed by the software package "Diffrac plus". The x-ray powder diffraction patterns of the individual crystalline Ibandronate polymorphs A and B are shown in FIGS. 1 and 4.

IR Measurement Method

Figure 5:
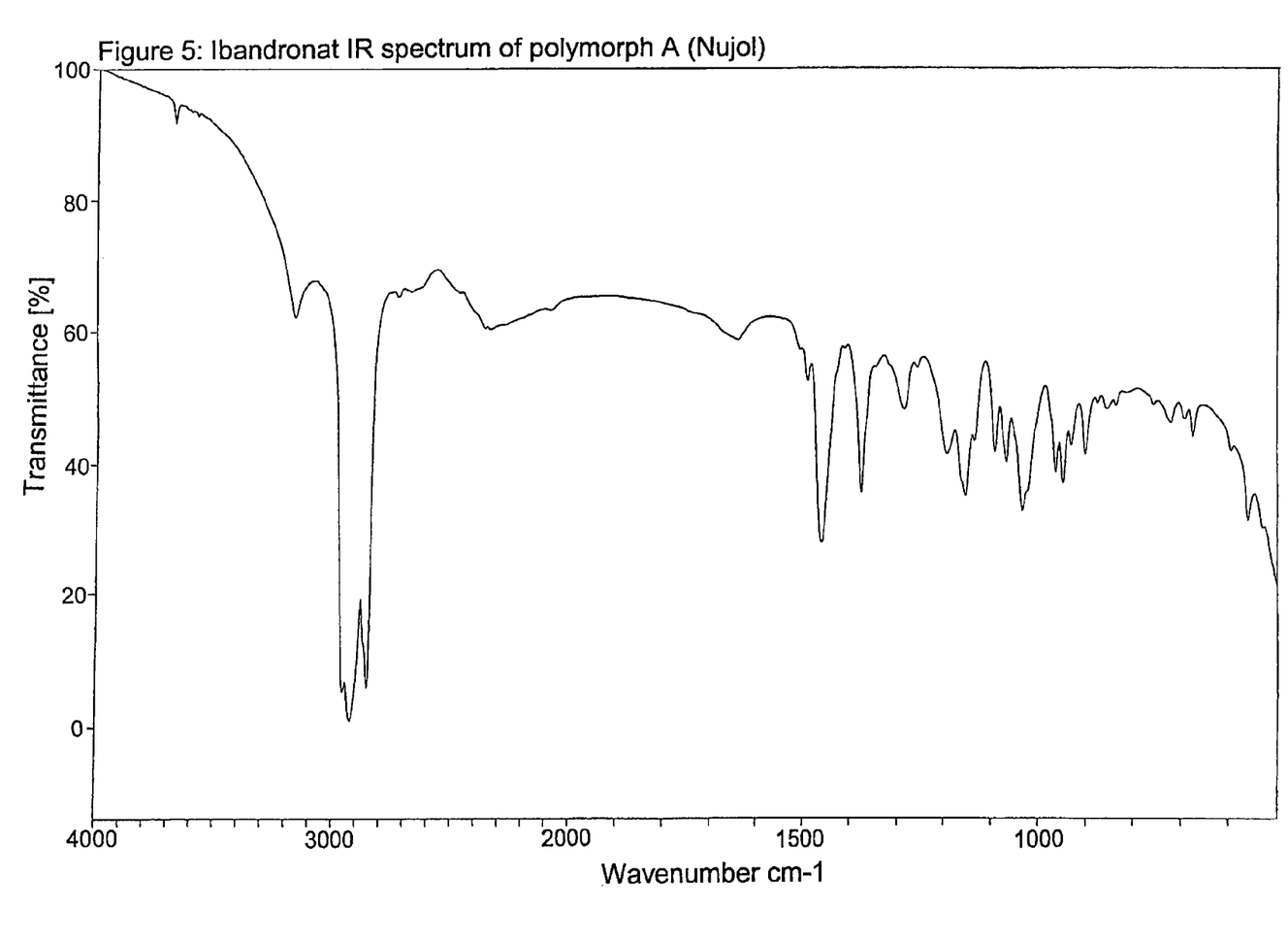
FIG. 5: shows an IR-spectrum of crystalline Ibandronate polymorph A

The IR spectra of the individual crystalline Ibandronate polymorphs A and B were recorded as film of Nujol suspension consisting of approx. 15 mg of sample in approx. 15 mg of Nujol between two sodium chloride plates. Measurements were carried out with an FT-IR spectrometer (IFS55 (Bruker) or equivalent instrument) in transmittance mode (resolution 4 cm$^{-1}$, detector: DTGS). The IR spectra of the individual crystalline Ibandronate polymorphs A and B are shown in FIGS. 2 and 5.

Raman Measurement Method

Figure 6:
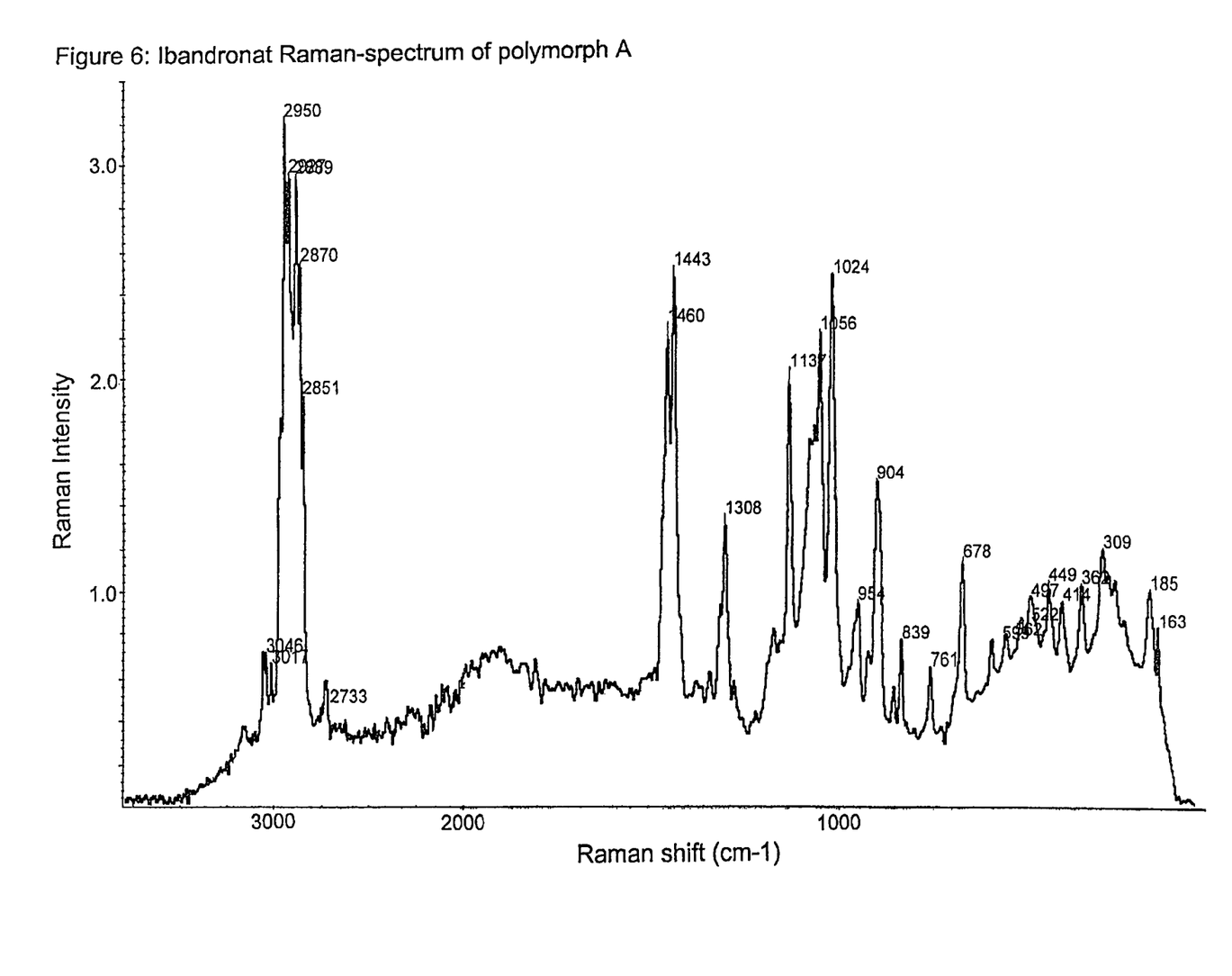
FIG. 6: shows a Raman spectrum of crystalline Ibandronate polymorph A

The Raman spectra of the individual crystalline Ibandronate polymorphs A and B were recorded as sample of about 20 mg of the powder and were filled into a glass tube (shortened NMR tube). The samples were measured with the FT-Raman of Nicolet coupled to a Magna 860 (Nicolet) in 90° scattering arrangement, detector: InGaAs. Measurement parameters resolution 8 cm$^{-1}$; laser power 0.95 W, No of scan 300. The FT-Raman spectra of the individual crystalline Ibandronate polymorphs A and B are shown in FIGS. 3 and 6.

Solubility Measurement

The solubility of the individual crystalline Ibandronate polymorphs A and B was measured for various solutions. Approximately 10 g of the corresponding polymorph A or B were suspended in three different buffer solutions at pH 2, pH 4 (Titrisol-buffer, citrate/HCl), at pH 7 (methenamine buffer, HCl) or in water. The suspension was stirred for 24 hours at 25° C. and was kept additonally 24 hours without stirring at the same temperature. Solubility was calculated by titration according to the following method.

The residue was filtered, 2 ml of the filtrate taken, 5 ml of Titriplex III solution were added and diluted with water to 100 ml. 2 ml of this solution were added to approximately 0.1 ml of xylenol orange indicator and the pH was adjusted to 6.5 by adding small portions of methenamine buffer solution or 0.1 M hydrochloric acid. The solution is titrated immediately with Th-DCTA-xylenol orange complex until the color changes from yellow to reddish-violet. The endpoint is determined photometrically.

Results are gathered in the following table.

|  | Polymorph A solubility in [g/l] | Polymorph B solubility in [g/l]* |
| --- | --- | --- |
| pH 2 | 280 | 274 |
| pH 4 | 276 | 278 |
| pH 7 | 292 | 299 |
| water | 278 | 279 | under at least partial conversion to polymorph A under at least partial conversion to polymorph A Reference Example 1

Preparation of 3-(N-methyl-N-pentyl) amino-1-hydroxypropane-1,1-diphosphonic acid monosodium salt 250 g (1.19 mol) N-methyl-N-pentyl-β-alanine hydrochloride, 233 g (2.84 mol) phosphorous acid, 151 ml (1.65 mol) phosphorous oxychloride and 900 ml diethyl carbonate were heated stepwise to 80° C. After 2 hours reaction time under continued heating the mixture was cooled to 60° C. and 1733 ml demineralized water were added, followed by azeotropic distillation of diethyl carbonate/water at 90 to 101° C. 358 ml demineralized water were added, the mixture was refluxed and water was distilled off. 316 ml demineralized water were added and water was distilled off twice. Finally 2040 ml demineralized water were added and the residue was cooled to 24° C. The pH was adjusted at 23° C. with sodium hydroxide solution (50%) to 4.4. Thereafter, 1100 ml ethanol were added to start crystallization. The suspension was stirred for 8 hours at 21 to 22° C. Then the solid was separated, washed with 344 ml cold ethanol/demineralized water (7/5 V/V), subsequently with 344 ml acetone/demineralized water (5/2 V/V) and dried at 60° C. 315.6 g (73.7%) of the title product were obtained in the form of colorless crystals.

Assay (complexometric titration): 100.6% (calculated on the anhydrous and solvent free basis) Residual solvents: 2.3% ethanol (GC)

3.9% water (KF)

Reference Example 2

Preparation of Crystalline Ibandronate Polymorph A 150 g 3-(N-methyl-N-pentyl) amino-1-hydroxypropane-1,1-diphosphonic acid monosodium salt (obtained according to reference example 1), were dissolved in 390 ml demineralized water at about 70-90° C. 205 ml water were distilled off. After filtration the filtrate was cooled to 60° C. and stirred for 45 minutes. Crystallization was initiated by means of crystalline polymorph A. After crystallization a mixture of demineralized water/acetone (290 ml/518 ml) previously heated to 50° C. was added under stirring. Thereafter, the suspension was cooled to about 20-25° C. under stirring, until the crystallization was complete. The product was separated and washed with a mixture of 50 ml acetone/demineralized water in a ratio of 1:1 (V/V). The product was dried for 48 hours in a vacuum from 150 to 20 mbar at 60° C.

Yield: 85 %

Identified with x-ray powder diffraction as crystalline Ibandronate polymorph A. (FIG. 4)

Assay (complexometric titration): 101.0% (calculated on the anhydrous and solvent free basis)

Example 1

Preparation of Crystalline Ibandronate Polymorph B 55 g of 3-(N-methyl-N-pentyl) amino-1-hydroxypropane-1,1-diphosphonic acid monosodium salt (obtained according to reference example 1) were dissolved in 240 ml demineralized water. 75 ml water were distilled off. After filtration, the remaining solution was brought to 35° C. and 190 ml acetone were added in 20 minutes. Thereafter, the mixture was cooled until ≦25° C. under stirring, up to the complete crystallization. The product was separated and washed with a mixture of acetone/demineralized water in a ratio of 1:1 (V/V). The product was dried in vacuum from 150 to 20 mbar for 12 hours at 40° C. and 24 hours at 60° C.

Yield: 81 %

Identified with x-ray powder diffraction as crystalline Ibandronate polymorph B. (FIG. 1)

Example 2

Preparation of Crystalline Ibandronate Polymorph B 55 g of 3-(N-methyl-N-pentyl) amino-1-hydroxypropane-1,1-diphosphonic acid monosodium salt (obtained according to reference example 1) were dissolved in 240 ml demineralized water. 75 ml water were distilled off. After filtration, the remaining solution was brought to 35° C., then 47 ml acetone were added and crystallization was initiated by means of 0.5 g crystalline Ibandronate polymorph B followed by addition of 144 ml acetone. Thereafter, the mixture was cooled until ≦25° C. under stirring in order to obtain a complete crystallization. The product was separated and washed with a mixture of acetone/demineralized water in a ratio of 1:1 (V/V). The product was dried in vacuum of 150 to 20 mbar at 40° C. for 12 hours and at 60° C. for 24 hours.

Yield: 82%

Identified with x-ray powder diffraction as crystalline Ibandronate polymorph B. (FIG. 1)

Example 3

Preparation of Crystalline Ibandronate Polymorph B 55 g of 3-(N-methyl-N-pentyl) amino-1-hydroxypropane-1,1-diphosphonic acid monosodium salt (obtained according to reference example 1) were dissolved in 240 ml demineralized water. 75 ml water were distilled off. After filtration, the remaining solution was brought to 35° C. and 382 ml acetone were added in 20 minutes and in parallel 0.5 g crystalline Ibandronate polymorph B were added. Thereafter, the mixture was cooled until ≦25° C. under stirring in order to obtain a complete crystallization. The product was separated and washed with a mixture of acetone/demineralized water in a ratio of 1:1 (V/V). The product was dried in vacuum of 150 to 20 mbar at 40° C. for 12 hours and at 60° C. for 24 hours.

Yield: 88 %

Identified with x-ray powder diffraction as crystalline Ibandronate polymorph B. (FIG. 1)

Example 4

Preparation of Crystalline Ibandronate Polymorph B 55 g Ibandronate monosodium salt, (obtained according to reference example 1) were dissolved in 240 ml demineralized water. 75 ml water was distilled off. After filtration, the remaining solution was brought to 35° C. and 190 ml Tetrahydrofuran (THF) was added in 20 minutes. Thereafter, the mixture was cooled until ≦25° C. under stirring, up to the complete crystallization. The product was separated and washed with 20 ml of THF. The product was dried in vacuum from 150 to 10 mbar for 12 hours at 40° C. and 24 hours at 60° C.

Yield: 82%

Identified with x-ray powder diffraction as crystalline Ibandronate polymorph B. (FIG. 1)

Example 5

Preparation of Crystalline Ibandronate Polymorph B 55 g Ibandronate monosodium salt, (obtained according to reference example 1) were dissolved in 240 ml demineralized water. 75 ml water was distilled off. After filtration, the remaining solution was brought to 35° C., then 47 ml of Tetrahydrofuran (THF) were added and crystallization initiates by means of 0.5 g Ibandronate crystal modification B followed by addition of 143 ml THF. Thereafter, the mixture was cooled until ≦25° C. under stirring in order to obtain a complete crystallization. The product was separated and washed with 20 ml of THF. The product was dried in vacuum of 150 to 10 mbar at 40° C. for 12 hours and at 60° C. for 24 hours.

Yield: 79%

Identified with x-ray powder diffraction as crystalline Ibandronate polymorph B. (FIG. 1)

Example 6

Preparation of Ibandronate Monosodium Salt, Monohydrate, Polymorph B 55 g Ibandronate monosodium salt, (obtained according to reference example 1) were dissolved in 240 ml demineralized water. 75 ml water was distilled off. After filtration, the remaining solution was brought to 55° C. and 190 ml of Tetrahydrofuran (THF) were added in 1 h. Thereafter, the mixture was cooled until ≦25° C. under stirring in order to obtain a complete crystallization. The product was separated and washed with 20 ml of THF. The product was dried in vacuum of 150 to 10 mbar at 40° C. for 12 hours and at 60° C. for 24 hours.

Yield: 78,5%

Identified with x-ray powder diffraction as crystalline Ibandronate polymorph B. (FIG. 1)

The invention claimed is:

1. A process for the preparation of a crystalline ibandronate polymorph B having an X-ray powder diffraction pattern having characteristic peaks expressed in angle 2-theta at approximately

| Angle 2-theta |
| --- |
| 9.7° |
| 12.2° |
| 14.4° |
| 16.8° |
| 25.8° | comrising dissolving 3-(N-methyl-N-pentyl) amino-1-hydroxypropane -1,1-diphosphonic acid monosodium salt, a monohydrate, a polymorph or a mixture of polymorphs thereof at a temperature between 10° C. and 45° C. in a polar solvent and adding a polar aprotic solvent to initialize the crystallization.

2. The process according to claim 1, wherein the temperature is 35° C., the polar solvent is water, and the polar aprotic solvent is an aliphatic ketone.

3. The process according to claim 2, wherein the aliphatic ketone is acetone.

4. The process according to claim 1, wherein the temperature is 35° C., the polar solvent is water, and the polar aprotic solvent is tetrahydrofuran.

5. A process for the preparation of a crystalline Ibandronate polymorph B having an X-ray powder diffraction pattern having characteristic peaks expressed in angle 2-theta at approximately

| Angle 2-theta |
| --- |
| 9.7° |
| 12.2° |

-continued

| Angle 2-theta |
| --- |
| 14.4° |
| 16.8° |
| 25.8° | comprising dissolving 3-(N-methyl-N-pentyl) amino-1-hydroxypropane-1,1-diphosphonic acid monosodium salt, a monohydrate, a polymorph or a mixture of polymorphs thereof at a temperature from 10° C. to 55° C. in a polar solvent and adding a cyclic ether to initialize the crystallization.

6. The process according to claim 5 wherein the cyclic ether is tetrahydrofuran.

* * * * *